(12) United States Patent
Forbes (10) Patent No.: US 10,702,548 B2
(45) Date of Patent: Jul. 7, 2020

(54) COMPOSITIONS AND METHODS FOR TREATING DRUG ADDICTION

(71) Applicant: Arnold Forbes, La Montagne (FR)

(72) Inventor: Arnold Forbes, La Montagne (FR)

(73) Assignee: Joelle Michele Forbes, Reunion (FR)

( * ) Notice: Subject to any disclaimer, the term of this patent is extended or adjusted under 35 U.S.C. 154(b) by 0 days.

(21) Appl. No.: 15/555,803

(22) PCT Filed: Mar. 4, 2016

(86) PCT No.: PCT/IB2016/000231
§ 371 (c)(1),
(2) Date: Sep. 5, 2017

(87) PCT Pub. No.: WO2016/139530
PCT Pub. Date: Sep. 9, 2016

(65) Prior Publication Data
US 2018/0064755 A1   Mar. 8, 2018

Related U.S. Application Data (60) Provisional application No. 62/128,352, filed on Mar. 4, 2015.

(51) Int. Cl.
| | | |
|---|---|---|
| *A61K 33/14* | (2006.01) |
| *A61K 45/06* | (2006.01) |
| *A61K 9/20* | (2006.01) |
| *A61K 9/24* | (2006.01) |
| *A61K 9/48* | (2006.01) |
| *A61K 33/24* | (2019.01) |
| *A61K 9/00* | (2006.01) |
| *A61P 25/30* | (2006.01) |

(52) U.S. Cl.
CPC ............ *A61K 33/14* (2013.01); *A61K 9/0095* (2013.01); *A61K 9/209* (2013.01); *A61K 9/2054* (2013.01); *A61K 9/4866* (2013.01); *A61K 9/4891* (2013.01); *A61K 33/24* (2013.01); *A61K 45/06* (2013.01); *A61P 25/30* (2018.01); *A61K 2300/00* (2013.01)

(58) Field of Classification Search
CPC .... A61K 2300/00; A61K 33/14; A61K 33/24; A61K 45/06; A61K 9/0095; A61K 9/2054; A61K 9/209; A61K 9/4866; A61K 9/4891; A61P 25/30
See application file for complete search history.

(56) References Cited

U.S. PATENT DOCUMENTS

| | | | |
|---|---|---|---|
| 4,322,407 A | 3/1982 | Ko | |
| 4,582,705 A * | 4/1986 | Primes | A61K 33/04 424/632 |
| 6,011,061 A | 1/2000 | Lai | |
| 7,429,580 B2 | 9/2008 | Gadde | |
| 8,815,304 B2 | 8/2014 | Forbes | |
| 2002/0048596 A1* | 4/2002 | Cevc | A61K 9/127 424/450 |
| 2002/0064566 A1 | 5/2002 | Beckett | |
| 2006/0008908 A1 | 1/2006 | Giles | |
| 2006/0160750 A1 | 7/2006 | Krishnan | |
| 2008/0113026 A1* | 5/2008 | McKinney | A61K 9/209 424/472 |
| 2011/0244055 A1* | 10/2011 | Forbes | A61K 33/14 424/606 |

FOREIGN PATENT DOCUMENTS

| | | |
|---|---|---|
| AU | 2046488 B2 | 7/1992 |
| EP | 0111144 A1 | 6/1984 |
| EP | 0305097 A2 | 3/1989 |
| WO | 2002069955 A1 | 9/2002 |
| WO | 2006014578 A2 | 2/2006 |
| WO | 200814044 A1 | 11/2008 |

OTHER PUBLICATIONS

Linter et al (British Journal of Hospital Medicine, Dec. 1985, pp. 361-365) (Year: 1985).*
Bulaev et al (Plenum Publishing Corporation, 1978, pp. 883-885) (Year: 1978).*
Chouinard et al (Communications in Psychopharmacology, 1977, vol. 1, pp. 373-383) (Year: 1997).*
Schrauzer et al., Lithium:Occurrence, Dietary Intakes, Nutritional Essentiality, Journal of the American College of Nutrition, 21:14-21 (2002).
Smith et al., Lithium in the brines of Fish Lake Valley and Columbus Salt Marsh, Nevada, United States Department of the Interior Geological Survey, pp. 1-22 (1977).
Casacchia et al., Rubidium Chloride in Chronic Mood Disorders, Recurrent Mood Disorders, pp. 286-290 (1993).
Neulieb, Effect of oral intake of cesium chloride: a single case report, Pharmacol. Biochem. Behav., 21: Suppl. 1, pp. 15-16 (1984)(PUBMED online, file MEDLINE, PMID 6522428).
Beck et al., Studies on the mechanism of rubidium-induced kaliuresis, Kidney International, 36:175-182 (1989).
Kazes et al., Eating Behaviour and Long-Term Lithium Treatment, Lithium, 4:125-133 (1993).
U.S. Office Action from U.S. Appl. No. 13/075,904, dated Mar. 12, 2013.
U.S. Office Action from U.S. Appl. No. 13/075,904, dated Nov. 7, 2013.
International Search Report from international Appl. No. PCT/IB2016000231, dated Sep. 27, 2016.
Tomkiewicz et al., Lithium treatment reduces morphine self-administration in addict rats, Nature, 252:227-229 (1974).
Wu et al., Design and evaluation of sustained release microspheres of potassium chloride prepared by Eudragit, European Journal of Pharmaceutical Sciences, 19:115-122 (2003).

(Continued)

*Primary Examiner* — Mark V Stevens
(74) *Attorney, Agent, or Firm* — Nevrivy Patent Law Group P.L.L.C.

(57) ABSTRACT

The present invention relates to a method of treating drug addiction in an individual in need thereof, comprising administering to the individual an effective amount of one or more alkali metals selected from the group consisting of one or more sources of cesium, one or more sources of rubidium, one or more sources of lithium, and combinations thereof. The present invention further relates to compositions comprising one or more alkali metals.

13 Claims, 2 Drawing Sheets

(56) References Cited

OTHER PUBLICATIONS

Alexander et al., Alcohol consumption in rats treated with lithium carbonate or rubidium chloride, Pharmacology Biochemistry and Behavior, 8:533-536 (1978).

* cited by examiner

COMPOSITIONS AND METHODS FOR TREATING DRUG ADDICTION

BACKGROUND OF THE INVENTION

1. Field of the Invention

The field of the invention relates to drug addition, more particularly, to methods and compositions for treating drug addiction.

2. Description of the Related Art

Drug addiction is a dependence on an illegal drug or a medication. Individuals who are addicted to drugs or medications may not be able to control the drug use and may continue using the drug despite the harm it causes. Drug addiction can cause an intense craving for the drug.

For many people, what starts as casual use leads to drug addiction. Drug addiction can cause serious, long-term consequences, including problems with physical and mental health, relationships, employment and the law. When a person repeatedly takes a natural substance such as opium, cocaine, or marijuana, or takes a specific drug such as heroin, barbiturates, or stimulants, it is nearly impossible to suddenly withhold the drug. Then, their major goal in life tends to focus on obtaining these substances and drugs.

As with many other conditions and diseases, vulnerability to addiction differs from person to person. Genes, mental health, family and social environment all play a role in addiction. Risk factors that can increase vulnerability include: family history of addiction; abuse, neglect, or other traumatic experiences in childhood; mental disorders such as depression and anxiety; early use of drugs; and method of administration—smoking or injecting a drug may increase its addictive potential.

Addiction is a complex disorder characterized by compulsive drug use. While each drug produces different physical effects, all abused substances share one thing in common: repeated use can alter the way the brain looks and functions. Taking a recreational drug causes a surge in levels of dopamine in the brain, which trigger feelings of pleasure. The brain remembers these feelings and wants them repeated. In an individual becomes addicted, the substance takes on the same significance as other survival behaviors, such as eating and drinking. Changes in the brain can interfere with the ability to think clearly, exercise good judgment, control your behavior, and feel normal without drugs. The uncontrollable craving to use grows more important than anything else, including family, friends, career, and even the individual's own health and happiness. The urge to use can be so strong that that the mind finds many ways to deny or rationalize the addiction.

The individual addicted to drugs may have the desire to quit, but most individuals will find that they can't do it on their own. Individuals who are afflicted may need help from their doctor, family, friends, support groups or an organized treatment program to overcome the drug addiction and stay drug-free. Depending on the level of addiction, the individual may need steps to help withdraw from using the drug (detoxification). However, in spite of the many available approaches to treat drug addition, addiction and relapse remain very significant problems.

Accordingly, there exists a need for new, effective drug addiction treatments which are accompanied by few adverse or undesirable side effects or less serious side effects.

BRIEF SUMMARY OF THE INVENTION

It is to be understood that both the foregoing general description of the embodiments and the following detailed description are exemplary, and thus do not restrict the scope of the embodiments.

The above and other objectives, as will be apparent to those having ordinary skill in the art, have been achieved by the present inventor by providing methods for treating drug addiction using one or more alkali metals.

In one aspect, the invention provides a method for treating drug addiction in an individual in need thereof, comprising administering to the individual per 24 hour period an effective amount of one or more alkali metals selected from the group consisting of one or more sources of cesium, one or more sources of rubidium, one or more sources of lithium, and combinations thereof.

The invention advantageously provides convenient and safe methods for treating drug addiction in an individual. Being addicted to drugs poses major health risks for individuals, and methods described herein are highly beneficial in that numerous associated diseases and attendant conditions caused by drug addiction can be prevented or ameliorated. This, in turn, can prevent pain, suffering, and even death caused by drug addiction as well as significantly reduce health care costs associated with drug addiction.

In another aspect, the invention encompasses compositions useful for treating drug addiction in an individual. The compositions comprise one or more alkali metals useful in carrying out the methods of the present invention as described herein.

In another aspect, the invention encompasses liquid compositions useful for treating drug addiction, comprising one or more alkali metals selected from the group consisting of one or more sources of cesium, one or more sources of rubidium, one or more sources of lithium, and combinations thereof.

In another aspect, the invention encompasses controlled release compositions useful for treating drug addiction, comprising one or more alkali metals selected from the group consisting of one or more sources of cesium, one or more sources of rubidium, one or more sources of lithium, and combinations thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE INVENTION

Unless otherwise noted, technical terms are used according to conventional usage. For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the word "about" means±10% of the numerical value.

In some embodiments, the invention is directed to methods and compositions for treating drug addiction in an individual in need thereof. In some embodiments, the methods comprise administering to the individual per 24 hour period an effective amount of one or more alkali metals selected from the group consisting of one or more sources of cesium, one or more sources of rubidium, one or more sources of lithium, and combinations thereof. In some embodiments, the methods comprise administering a composition that is a controlled release oral dosage form with an effective amount of one or more alkali metals selected from the group consisting of one or more sources of cesium, one or more sources of rubidium, one or more sources of lithium, and combinations thereof.

The phrase "effective amount" as used herein refers to the amount of an alkali metal or combinations thereof of the invention which is effective for producing the desired effect in treating drug addiction upon administration to an individual or patient. The desired effect is reducing cravings associated with drug use and addiction.

The drug addiction to be treated is not limiting. In some embodiments, the drug addiction is caused by an illegal drug or a legal medication. In some embodiments, the drug causing addiction is selected from nicotine, alcohol, opioid receptor agonists (such as morphine, opiates, codeine, opium heroin), stimulants (such as amphetamine and methamphetamine), cocaine, crack, central nervous system sedatives such as the barbiturates (phenobarbital, pentobarbital, thiopental, and the like), hashish, marijuana, hallucinogens, khat, organic solvents, methylene-dioxy-methamphetamine, flunitrazepam, and gamma-hydroxybutyrate, benzodiazepines (for example, diazepam, lorazepam, oxazepam, chlordiazepoxide, and the like).

In some embodiments, the methods and compositions are useful for treating psychic dependence. In some embodiments, the methods and compositions are useful for treating physical dependence. In some embodiments, the methods and compositions are useful for treating psychic and physical dependence.

In some embodiments, the source of cesium administered has total cesium content in an amount of about 40 milligrams to about 1500 milligrams. In some embodiments, the source of cesium administered has total cesium content that ranges from about 40-1250 milligrams, from about 40-1000 milligrams, from about 40-750 milligrams, from about 60-500 milligrams, from about 80-400 milligrams, from about 100-300 milligrams, or from about 150-250 milligrams. In some embodiments, the total cesium content is about 40 milligrams, about 50 milligrams, about 60 milligrams, about 75 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, about 1350 milligrams, about 1400 milligrams, about 1450 milligrams, or about 1500 milligrams.

In some embodiments, the source of cesium is elemental cesium, one or more cesium compounds, cesium ions, salts of cesium, or combinations thereof. In some embodiments, the source is one or more salts of cesium having total cesium content in an amount of about 40 milligrams to about 1500 milligrams. In some embodiments, the one or more salts of cesium is selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$).

In some embodiments, the salt of cesium is cesium chloride and the salt is administered in an amount of about 50 milligrams to about 1900 milligrams (total cesium content of about 40 to about 1500 milligrams). In some embodiments, the salt is administered in an amount of about 50-1700 milligrams, from about 50-1500 milligrams, from about 50-1200 milligrams, from about 75-1000 milligrams, from about 100-800 milligrams, from about 200-600 milligrams, or from about 300-500 milligrams. In some embodiments, about 50 milligrams, about 75 milligrams, about 100 milligrams, about 200 milligrams, about 300 milligrams, about 400 milligrams, about 500 milligrams, about 600 milligrams, about 700 milligrams, about 800 milligrams, about 900 milligrams, about 1000 milligrams, about 1100 milligrams, about 1200 milligrams, about 1300 milligrams, about 1400 milligrams, about 1500 milligrams, about 1600 milligrams, about 1700 milligrams, about 1800 milligrams or about 1900 milligrams of cesium chloride is administered.

In some embodiments, the source of rubidium has total rubidium content in an amount of about 35 milligrams to about 1350 milligrams. In some embodiments, the source of rubidium administered has total rubidium content that ranges from about 35-1250 milligrams, from about 35-1000 milligrams, from about 35-750 milligrams, from about 50-500 milligrams, from about 80-400 milligrams, from about 100-300 milligrams, or from about 150-250 milligrams. In some embodiments, the total rubidium content is about 35 milligrams, about 45 milligrams, about 50 milligrams, about 70 milligrams, about 90 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, or about 1350 milligrams.

In some embodiments, the source of rubidium is elemental rubidium, one or more rubidium compounds, rubidium ions, salts of rubidium, or combinations thereof. In some embodiments, the one or more sources of rubidium are one or more salts of rubidium. In some embodiments, the total content of rubidium in the one or more salts of rubidium is in an amount of about 35 milligrams to about 1350 milligrams. In some embodiments, the one or more salts of rubidium is selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$). In some embodiments, the salt of rubidium is rubidium chloride.

In some embodiments, rubidium chloride is administered in an amount of about 50 milligrams to about 1900 milligrams (total rubidium content of about 35 milligrams to about 1350 milligrams). In some embodiments, the salt is administered in an amount of about 50-1700 milligrams, from about 50-1500 milligrams, from about 50-1200 milligrams, from about 75-1000 milligrams, from about 100-800 milligrams, from about 200-600 milligrams, or from about 300-500 milligrams. In some embodiments, about 50 milligrams, about 60 milligrams, about 70 milligrams, about 75 milligrams, about 90 milligrams, about 100 milligrams, about 200 milligrams, about 300 milligrams, about 400 milligrams, about 500 milligrams, about 600 milligrams, about 700 milligrams, about 800 milligrams, about 900 milligrams, about 1000 milligrams, about 1100 milligrams, about 1200 milligrams, about 1300 milligrams, about 1400 milligrams, about 1500 milligrams, about 1600 milligrams, about 1700 milligrams, about 1800 milligrams or about 1900 milligrams of rubidium chloride is administered.

In some embodiments, about 300 mg of rubidium chloride is administered per day. In some embodiments, rubidium chloride is administered from about 2 weeks to about 6 months, from about 1 month to about 4 months, or about 2 months.

In some embodiments, a combination of about 150 mg rubidium chloride and about 150 mg cesium chloride is administered per day. In some embodiments, the combination is administered from about 2 weeks to about 6 months, from about 1 month to about 4 months, or for about 2 months.

In some embodiments, the source of lithium has a total lithium content in an amount of about 0.3 milligrams to about 85 milligrams. In some embodiments, the source of lithium administered has total lithium content that ranges from about 0.3-380 milligrams, about 0.3-350 milligrams, about 0.3-300 milligrams about 0.3-250 milligrams, about 0.3-225 milligrams, about 0.3-200 milligrams, about 0.3-175 milligrams, about 0.3-150 milligrams, about 0.3-125 milligrams, about 0.3-100 milligrams, about 0.3-80 milligrams, from about 0.3-70 milligrams, from about 0.3-50 milligrams, from about 1-40 milligrams, from about 3-35 milligrams, from about 5-30 milligrams, or from about 10-20 milligrams. In some embodiments, the total lithium content is about 0.5 milligrams, about 1 milligrams, about 5 milligrams, about 10 milligrams, about 15 milligrams, about 20 milligrams, about 25 milligrams, about 30 milligrams, about 35 milligrams, about 40 milligrams, about 45 milligrams, about 50 milligrams, about 55 milligrams, about 60 milligrams, about 65 milligrams, about 70 milligrams, about 75 milligrams, about 80 milligrams, or about 85 milligrams.

In some embodiments, the one or more sources of lithium is elemental lithium, one or more lithium compounds, lithium ions, lithium salts, or combinations thereof.

In some embodiments, the source of lithium is one or more lithium salts. In some embodiments, the total content of lithium in one or more lithium salts is in an amount of about 0.3 milligrams to about 400 milligrams. In some embodiments, the one or more lithium salts is selected from the group consisting of lithium acetate ($CH_3COOLi$), lithium acetylsalicylate, lithium aspartate, lithium benzoate ($C_6H_5COOLi$), lithium bitartrate, lithium bromide (LiBr), lithium carbonate ($Li_2CO_3$), lithium chloride (LiCl), lithium chromate ($LiCrO_4$), lithium citrate ($Li_3C_6H_5O_7$), lithium fluoride (LiF), lithium gluconate, lithium iodate ($LiIO_3$), lithium metaborate ($LiBO_2$), lithium nitrate ($LiNO_3$), lithium orotate ($LiC_5H_3N_2O_4$), lithium perchlorate ($LiClO_4$), lithium phosphate ($Li_3PO_4$), lithium selenite ($LiH_3(SeO_3)_2$), lithium succinate ($C_4H_5LiO_4$), lithium sulfate ($Li_2SO_4$), and lithium thenoate. In some embodiments, the one or more lithium salts is lithium aspartate, lithium carbonate, lithium citrate or lithium orotate, or combinations thereof.

In some embodiments, the source of lithium is lithium carbonate administered in an amount of about 10 milligrams to about 2000 milligrams. In some embodiments, lithium carbonate is administered in an amount of about 10-1850 milligrams, about 10-1500 milligrams, about 10-1250 milligrams, about 10-1000 milligrams, about 10-800 milligrams, about 10-600 milligrams, about 10-500 milligrams, about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium carbonate is administered.

In some embodiments, the source of lithium is lithium aspartate and is administered in an amount of about 10 milligrams to about 2000 milligrams. In some embodiments, lithium aspartate is administered in an amount of about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium aspartate is administered.

In some embodiments, the source of lithium is lithium citrate administered in an amount of about 10 milligrams to about 2000 milligrams. In some embodiments, lithium citrate is administered in an amount of about 10-1850 milligrams, about 10-1500 milligrams, about 10-1250 milligrams, about 10-1000 milligrams, about 10-800 milligrams, about 10-600 milligrams, about 10-500 milligrams, about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium citrate is administered.

In some embodiments, the source of lithium is lithium orotate administered in an amount of about 10 milligrams to about 2000 milligrams. In some embodiments, lithium orotate is administered in an amount of about 10-1850 milligrams, about 10-1500 milligrams, about 10-1250 milligrams, about 10-1000 milligrams, about 10-800 milligrams, about 10-600 milligrams, about 10-500 milligrams, about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium orotate is administered.

In some embodiments, the commercial source of cesium, rubidium or lithium for use in the present invention is in highly pure form. In some embodiments, the source is 95% pure, 96% pure, 97% pure, 98% pure, 99% pure, 99.5% pure, 99.9% pure, 99.999% pure or greater. Highly pure sources are known to persons of skill in the art and are commercially available. In some embodiments, such sources are non-toxic and pharmaceutically acceptable.

In some embodiments, the one or more alkali metals of the invention are administered substantially together with one or more sources of potassium to prevent a risk of potassium depletion in the individual. In some embodiments, the one or more sources of potassium is elemental potassium, potassium compounds, potassium ions, potassium salts, one or more potassium-rich foods, or combinations thereof. In some embodiments, the potassium-rich foods are selected from the group consisting of banana, raisins, spinach, pumpkin, tomato, broccoli, orange juice, milk, yams, potato, corn, yoghurt, cabbage, salmon, green barley essence, peanut butter, prunes cheese, peach lettuce, celery, ice cream, peas, grapes, pineapple, green beans, asparagus, apple, apricot, rice, onion, strawberries and bread (25% flour) and combinations thereof.

The alkali metals can be administered in a single dose or they can be spread out over several doses in a 24 hour period. In some embodiments, the one or more alkali metals are divided into several doses administered over a 24 hour period. In some embodiments, 2, 3, 4, 5, 6 or more doses are administered. In some embodiments, the one or more alkali metals are administered in a single dose in a 24-hour period.

In some embodiments, the alkali metal sources are the only active agents administered to the individual to treat drug addiction. In other embodiments, additional active agents are administered that treat drug addiction.

In some embodiments the individual to be treated or administered is a mammal. In some embodiments, the individual is a human. The effective amounts as described herein are contemplated for human administration, and can be adjusted as needed to accommodate administration to other species.

The duration of treatment or administration can vary for each individual to be treated/administered depending on the individual cases and the strength of the addiction. In some embodiments, it can be continuous for a period of several days, weeks, months, or years of treatment or can be intermittent where the individual is administered alkali metals for a period of time, followed by a period of time where they are not treated, and then a period of time where treatment resumes as needed to suppress drug addiction in the individual. For example, in some embodiments, the individual to be treated is administered the alkali metals of the invention daily, every other day, every three days, every four days, 2 days per week 3 days per week, 4 days per week, 5 days per week or 7 days per week. In some embodiments, the individual is administered the alkali metals for 1 week, 2 weeks, 3 weeks, 4 weeks, 1 month, 2 months, 3 months, 4 months, 5 months, 6 months, 7 months, 8 months, 9 months, 10 months, 11 months, 1 year or longer. In some embodiments, the individual is administered a dosage every morning with or after food and taken for two months until the addiction to the drug is lost. In some embodiments, individuals who are obese are administered the alkali metal of the invention every day for longer durations of time. In some embodiments, drug addicted patients are treated for 6 months or longer to achieve the desired effect.

In some embodiments, individuals addicted to codeine can be treated for addiction within one month, while treatments for strongly addictive drugs can last for several months to even years.

The combinations of alkali metal sources are administered substantially together. As used herein "substantially together" refers to administering to an individual more than one alkali metal sources in (i) a single dosage form, or (ii) separate dosage forms or a combination of compositions, such that, they are administered either simultaneously or within a period of time such that the subject receives benefit of the aggregate effects of the separate dosage forms or combination of compositions. In some embodiments, the alkali metal source combinations are administered as a single dose. In some embodiments, separate dosage forms for more than one alkali metal sources are administered within the same 24 hour period. In some embodiments, separate dosage forms for more than one alkali metal sources are administered within the same 12 hour period. In some combinations, separate dosage forms for more than one alkali metal sources are administered within the same 6 hour period. In some embodiments, separate dosage forms for more than one alkali metal sources are administered within the same 3-6 hour period. In some combinations, separate dosage forms for more than one alkali metal sources are administered within the same 1-3 hour period. In some combinations, separate dosage forms for more than one alkali metal sources are administered within the same one hour period. In some embodiments, the drug addiction suppressant effect achieved by a single dose in the morning is sufficient to halt drug cravings for the remainder of the day.

In some embodiments, the individual is administered a combination of alkali metals comprising cesium chloride, rubidium chloride and one or more sources of lithium selected from the group consisting of lithium orotate, lithium carbonate, lithium aspartate, lithium citrate and combinations thereof. In some embodiments, the cesium chloride is administered in an amount of about 50 milligrams to about 1900 milligrams or any specific amount or range as described herein, the rubidium chloride is administered in an amount of about 50 milligrams to about 1900 milligrams or any specific amount or range as described herein, the lithium orotate is administered in an amount of about 20 milligrams to about 200 milligrams or any specific amount or range as described herein, the lithium carbonate is administered in an amount of about 10 milligrams to about 450 milligrams or any specific amount or range as described herein, and the lithium aspartate is administered in an amount of about 10 milligrams to about 450 milligrams or any specific amount or range as described herein. In some embodiments, the lithium source includes at least two of: lithium orotate administered in an amount of about 10 milligrams to about 200 milligrams; lithium carbonate administered in an amount of about 10 milligrams to about 450 milligrams; or lithium aspartate administered in an amount of about 10 milligrams to about 450 milligrams. In some embodiments, the lithium orotate is administered in an amount of about 10 milligrams to about 200 milligrams, lithium carbonate is administered in an amount of about 10 milligrams to about 450 milligrams, and lithium aspartate is administered in an amount of about 10 milligrams to about 450 milligrams.

In some embodiments, one or more sources of cesium and lithium are administered to an individual in a single dose, i.e., substantially together. In some embodiments, the source of cesium is cesium chloride and the one or more sources of lithium is selected from the group consisting of lithium orotate, lithium carbonate, lithium citrate, lithium aspartate, and combinations thereof. In some embodiments, the cesium chloride is administered in an amount of about 50 milligrams to about 1900 milligrams or any specific amount or range as described herein. In some embodiments, the lithium orotate is administered in an amount of about 10 milligrams to about 200 milligrams or any specific amount or range as described herein. In some embodiments, the lithium carbonate is administered in an amount of about 10 milligrams to about 450 milligrams or any specific amount or range as described herein. In some embodiments, the lithium citrate is administered in an amount of about 10 milligrams to about 450 milligrams or any specific amount or range as described herein. In some embodiments, the lithium aspartate is administered in an amount of about 10 milligrams to about 450 milligrams or any specific amount or range as described herein. In some embodiments the lithium includes at least two of: lithium orotate administered in an amount of about 10 milligrams to about 200 milligrams or any specific amount or range as described herein; lithium carbonate administered in an amount of about 10 milligrams to about 450 milligrams or any specific amount or range as described herein; or lithium aspartate administered in an amount of about 10 milligrams to about 450 milligrams or any specific amount or range as described herein. In some embodiments, lithium orotate is administered in an amount of about 10 milligrams to about 200 milligrams; lithium carbonate is administered in an amount of about 10 milligrams to about 450 milligrams; and lithium aspartate is administered in an amount of about 10 milligrams to about 450 milligrams.

In some embodiments, one or more sources of rubidium and lithium are administered in a single dose. In some embodiments, the source of rubidium is rubidium chloride and the one or more sources of lithium is selected from the group consisting of lithium orotate, lithium citrate, lithium carbonate and lithium aspartate. In some embodiments, the rubidium chloride is administered in an amount of about 50 milligrams to about 1900 milligrams or any specific amount or range as described herein. In some embodiments, the amount of lithium orotate is administered in an amount of about 10 milligrams to about 200 milligrams or any specific amount or range as described herein. In some embodiments, the lithium citrate is administered in an amount of about 10 milligrams to about 450 milligrams or any specific amount or range as described herein. In some embodiments, the amount of lithium carbonate is administered in an amount of about 10 milligrams to about 450 milligrams or any specific amount or range as described herein. In some embodiments, the lithium aspartate is administered in an amount of about 10 milligrams to about 450 milligrams or any specific amount or range as described herein. In some embodiments, the lithium includes at least two of lithium orotate administered in an amount of about 10 milligrams to about 200 milligrams or any specific amount or range as described herein, lithium carbonate administered in an amount of about 10 milligrams to about 450 milligrams or any specific amount or range as described herein, or lithium aspartate administered in an amount of about 10 milligrams to about 450 milligrams or any specific amount or range as described herein. In some embodiments, lithium orotate is administered in an amount of about 10 milligrams to about 200 milligrams; lithium carbonate is administered in an amount of about 10 milligrams to about 450 milligrams; and lithium aspartate is administered in an amount of about 10 milligrams to about 450 milligrams.

In some embodiments, a combination of 150 milligrams of cesium chloride and 150 milligrams of rubidium chloride is administered. In some embodiments, a combination of 150 milligrams of cesium chloride, 150 milligrams of rubidium chloride and 40 milligrams of lithium carbonate is administered. In other embodiments, a combination of 150 milligrams of cesium chloride, 150 milligrams of rubidium chloride and 40 milligrams of lithium aspartate is administered.

In some embodiments, the invention is directed to drug addiction treatment compositions useful for treating drug addiction in an individual. In some embodiments, the compositions are pharmaceutical compositions.

In some embodiments, the invention is directed to compositions which are functional foods and/or beverages. The compositions comprise one or more alkali metals in amounts that are useful in carrying out the methods of the present invention as described herein.

In some embodiments, the drug addiction treatment compositions of the invention can be prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985), herein incorporated by reference in its entirety.

In some embodiments, the compositions of the invention are formulated in unit dosage form for ease of administration and uniformity of dosage. The term "unit dosage form" as used herein refers to physically discrete units suited as unitary dosages for the individuals to be treated. In some embodiments, the compositions are formulated into discrete dosage units each containing a predetermined "unit dosage" or "unit dose" of one or more active compounds calculated to produce the desired effect in association with the required pharmaceutical carrier.

In some embodiments, the compositions have a unit dose or amount of cesium of about 10 milligrams to about 1500 milligrams or any specific amount or range as described herein. In some embodiments, the unit dose or amount of cesium is about 20 milligrams, about 40 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, about 1350 milligrams, about 1400 milligrams, about 1450 milligrams, or about 1500 milligrams.

In some embodiments, the compositions have a unit dose or amount of rubidium of about 10 milligrams to about 1350 milligrams or any specific amount or range as described herein. In some embodiments, the unit dose or amount of rubidium is about 25 milligrams, about 35 milligrams, about 50 milligrams, about 75 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, or about 1350 milligrams.

In some embodiments, the compositions have a unit dose or amount of lithium of about 0.1 milligrams to about 85 milligrams or any specific amount or range as described herein. In some embodiments, the unit dose or amount of lithium is about 1 milligrams, about 1.5 milligrams, about 2 milligrams, about 5 milligrams, about 10 milligrams, about 15 milligrams, about 20 milligrams, about 25 milligrams, about 30 milligrams, about 35 milligrams, about 40 milligrams, about 45 milligrams, about 50 milligrams, about 55 milligrams, about 60 milligrams, about 65 milligrams, about 70 milligrams, about 75 milligrams, about 80 milligrams, or about 85 milligrams.

In some embodiments, the invention is directed to a drug addiction treatment composition or combination of compositions taken substantially together comprising: one or more salts of cesium having a combined content in an amount of about 40 milligrams to about 1500 milligrams or any specific amount or range as described herein; one or more salts of rubidium having a combined rubidium content in an amount of about 35 milligrams to about 1350 milligrams or any specific amount or range as described herein; one or more lithium salts having a combined lithium content in an amount of about 0.3 milligrams to about 85 milligrams or any specific amount or range as described herein; and combinations thereof.

In some embodiments, the drug addiction treatment composition or combination of compositions comprises one or more salts of cesium selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate ($(COOCs)_2$), cesium perchlorate ($CsClO_4$), cesium permanganate ($CsMnO_4$), cesium propionate ($C_2H_5CO_2Cs$) and cesium sulfate ($Cs_2O_4S$). In some embodiments, cesium chloride is present in an amount of about 50 milligrams to about 1900 milligrams.

In some embodiments, the drug addiction treatment composition or combination of compositions comprises one or more salts of rubidium selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$). In some embodiments, rubidium chloride is present in an amount of about 100 milligrams to about 1900 milligrams.

In some embodiments, the drug addiction treatment composition or combination of compositions comprises one or more salts of lithium selected from the group consisting of lithium acetate ($CH_3COOLi$), lithium acetylsalicylate, lithium aspartate, lithium benzoate ($C_6H_5COOLi$), lithium bitartrate, lithium bromide (LiBr), lithium carbonate ($Li_2CO_3$), lithium chloride (LiCl), lithium chromate ($LiCrO_4$), lithium citrate ($Li_3C_6H_5O_7$), lithium fluoride (LiF), lithium gluconate, lithium iodate ($LiIO_3$), lithium metaborate ($LiBO_2$), lithium nitrate ($Li\ NO_3$), lithium orotate ($LiC_5H_3N_2O_4$), lithium perchlorate ($LiClO_4$), lithium phosphate ($Li_3PO_4$), lithium selenite ($LiH_3(SeO_3)_2$), lithium succinate ($C_4H_5LiO_4$), lithium sulfate ($Li_2SO_4$), and lithium thenoate. In some embodiments, the lithium salt is lithium orotate, lithium carbonate, lithium aspartate, or combinations thereof. In some embodiments, lithium orotate is present in an amount from about 20 milligrams to about 200 milligrams. In some embodiments, lithium carbonate is present in an amount from about 10 milligrams to about 450 milligrams. In some embodiments, lithium aspartate is present in an amount from about 10 milligrams to about 450 milligrams.

In some embodiments, the drug addiction treatment composition or combination of compositions includes at least two of: lithium orotate in an amount of about 20 milligrams to about 200 milligrams; lithium carbonate in an amount of about 20 milligrams to about 450 milligrams, or lithium aspartate in an amount of about 20 milligrams to about 450 milligrams.

In some embodiments, the drug addiction treatment composition or combination of compositions includes lithium orotate in an amount of about 20 milligrams to about 200 milligrams; lithium carbonate in an amount of about 10 milligrams to about 450 milligrams, and lithium aspartate in an amount of about 10 milligrams to about 450 milligrams.

Pharmaceutically acceptable carriers and excipients are those that are compatible with the other ingredients in the formulation and biologically acceptable. The alkali metal can be provided in combination with a pharmaceutically acceptable carrier, excipients or diluent. Suitable carriers, excipients and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The alkali metals can also be administered pure in sachets that have to be added to a glass of water and then drunk.

The compositions according to the invention for use in the aforementioned methods may be administered by any convenient method, for example by oral (including by inhalation), parenteral, mucosal (e.g. buccal, sublingual, nasal), rectal, subcutaneous or transdermal administration and the compositions adapted accordingly.

In some embodiments, the drug addiction treatment composition is suitable for oral administration. In some embodiments, the drug addiction treatment composition is a tablet, capsule, pill, dragee, suspension, lozenge, emulsion, aqueous solution, liquid, gel, or syrup. In some embodiments, the compositions can be delivered in the form of functional foods and/or beverages, as well as in the form of various supplements.

A liquid formulation or liquid composition will generally comprise a suspension or solution of the one or more alkali metals or salts in a suitable aqueous or non-aqueous liquid carrier(s), for example, water, ethanol, glycerine, polyethylene glycol or an oil. In some embodiments, the composition formulation or composition may also contain a suspending agent, preservative, flavoring or coloring agent. In some embodiments, the drug addiction treatment composition in the form of a solution can further comprise one or more vitamins, minerals, electrolytes and combinations thereof.

In some embodiments, the drug addiction treatment composition comprises one or more of the following alkali metals and amounts: a source of rubidium having a total rubidium content in an amount of about 35 milligrams to about 1350 milligrams or any specific amount of rubidium or range as described herein, a source of cesium having a total cesium content in an amount of about 40 milligrams to about 1500 milligrams or any specific amount of cesium or range as described herein, and a source of lithium having a total lithium content in an amount of about 0.3 milligrams to about 85 milligrams or any specific amount of lithium or range as described herein.

In some embodiments, the liquid composition comprises one or more of the following alkali metals and amounts: rubidium chloride in an amount of about 50 milligrams to about 1900 milligrams or any specific amount or range of rubidium chloride as described herein, cesium chloride in an amount of about 50 milligrams to about 1900 milligrams or any specific amount or range of cesium chloride as described herein, and one or more of lithium orotate, lithium aspartate, and lithium carbonate in an amount of about 20 milligrams to about 200 milligrams or any specific amount or range of lithium orotate, lithium aspartate, and lithium carbonate as described herein. In some embodiments, electrolytes such as potassium, for example, are included, which in correct physiological quantities can increase the efficiency of the body to utilize glycogen and improve muscular activities. In some embodiments, the electrolytes comprise sodium, potassium, chloride, magnesium, bicarbonate or a combination thereof. In some embodiments, the source of potassium in the beverage compositions is potassium chloride. In some embodiments, potassium other than in the form of potassium chloride, such as potassium citrate, gluconate, carbonate or phosphate, may induce potassium deficiency and alkalosis. A depletion of potassium can lead to a decrease in action potential of muscle and can also cause metabolic alkalosis. Certain beverage embodiments overcome this problem.

In some embodiments, carbohydrates can be added, including sucrose, glucose, citrate or a combination thereof. In some embodiments, one or more carbohydrates are added with one or more electrolytes. In some embodiments, the unpleasant taste of electrolytes in drinks can be masked by carefully balancing the relative ratios of the electrolytes.

In some embodiments, the liquid composition can comprise a combination of water, one or more alkali metals, carbohydrates, and electrolytes, such as sodium, potassium, chloride, magnesium and/or bicarbonate. In some embodiments, the liquid composition can further comprise one or more of high fructose corn syrup, artificial colors and flavors. In some embodiments, the carbohydrate is glucose, fructose, dextrose, sucrose or a combination thereof. In some embodiments, the beverage comprises taurine and/or glucuronolactone.

In some embodiments, the liquid composition comprises a combination of disodium hydrogen phosphate ($Na_2HPO_4.12H_2O$), sucrose, dextrose, rubidium chloride, potassium chloride, magnesium sulfate, sodium citrate, sodium acid phosphate, ascorbic acid, pyridoxine hydrochloride, citric acid, and sodium chloride. In some embodiments, artificial sweeteners, colorings, vitamins, minerals, preservatives and combinations thereof may be incorporated.

When in powder form, the composition of one or more alkali base metals may be provided as small crystals. In some embodiments, the powder composition may be prepared by simply admixing the appropriate reactant ingredients and packaging them in conventional beverage containers used for such purposes. In some embodiments, the liquid carrier used on-demand to form the fluid beverage may be distilled, deionized, carbonated, or mineral water, and the liquid may also contain a small amount of nonglucose or low glycemic index sweetener (such as aspartame or sucralose) to impart a pleasant sweet taste to the prepared beverage. In some embodiments, such a fluid beverage will have a total caloric load not to exceed 60 kcal per serving, and optionally is flavored with one or more natural and artificial sweeteners, either individually or in combination, in their usual proportions. The resulting fluid beverage can be initially preserved by pasteurization or cold sterilization. In some embodiments, the beverage is consumed at an average volume intake of less than one liter per day.

In some embodiments, the dry composition (of chosen ingredients) can be mixed at will with a very small amount of water (for example, less than 30 ml) to produce a mixture which may later be diluted to provide multiple units in the proper dose amounts, or can be poured into capsule form, designed for optimum portability in situations requiring little weight or baggage.

It is to be appreciated that the dry composition of one or more alkali base metals is water soluble which allows a host of delivery options.

In addition, the drug addiction treatment composition may be kept as a dry powder mixture (for example in sachets) for an indefinite time period without degradation. Then, at a chosen later time, the dry powder can be combined with water or another aqueous based liquid, and optionally a small amount of non-glucose or low glycemic index sweetener such as aspartame or sucralose to impart a pleasant sweet taste for the beverage. In some embodiments, the beverage will have a total caloric value not to exceed 60 kcal per serving, after being properly constituted as a ready to drink fluid.

Optionally, the dry particle admixture may be flavored with one or more natural and/or artificial favoring aids or sweeteners, either individually or in combination, in their usual proportions. The powder can then be packaged in individual moisture and tamper-resistant packaging available commercially for such purposes.

In some embodiments, the drug addiction treatment compositions and oral dosage forms of the invention can additionally be formulated with vitamins and minerals, including to compensate for any loss thereof due to a reduced food intake by the individual. In some embodiments, a multivitamin and mineral supplement is administered separately from the pharmaceutical composition. Multivitamin and mineral supplements are well known. Such supplements typically contain vitamins A, B1, B2, B6, B12, C, D, E, folic acid, calcium, iron, magnesium and zinc. Amino acids may also be included to supplement the daily protein requirement.

In some embodiments of the invention, the composition is a parenteral composition. Typical parenteral compositions consist of a solution or suspension of the alkali metal in a sterile aqueous or non-aqueous carrier or parenterally acceptable oil, for example polyethylene glycol, polyvinyl pyrrolidone, lecithin, *arachis* oil or sesame oil. Alternatively, the solution can be lyophilised and then reconstituted with a suitable solvent just prior to administration.

Compositions of the invention for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container can be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions of the invention suitable for buccal or sublingual administration include tablets, lozenges and pastilles, wherein the active ingredient is formulated with a carrier such as sugar and acacia, tragacanth, or gelatin and glycerin. Compositions of the invention for rectal or vaginal administration are conveniently in the form of suppositories (containing a conventional suppository base such as cocoa butter), pessaries, vaginal tabs, foams or enemas. Compositions of the invention suitable for transdermal administration include ointments, gels, patches and injections including powder injections.

In some embodiments, the drug addiction treatment composition is a controlled release oral dosage form comprising an effective amount of one or more alkali metals. In some embodiments, the effective amount of one or more alkali metals is selected from the group consisting of one or more sources of cesium, one or more sources of rubidium, one or more sources of lithium, and combinations thereof. In some embodiments, the one or more sources of cesium has a total cesium content in an amount of about 40 milligrams to about 1500 milligrams, the one or more sources of rubidium has a total rubidium content in an amount of about 35 milligrams to about 1350 milligrams, and the one or more sources of lithium has a total lithium content in an amount of about 0.3 milligrams to about 400 milligrams.

In some embodiments, the source of cesium is one or more salts of cesium. The one or more salts of cesium may be selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$).

In some embodiments, the one or more sources of rubidium is one or more salts of rubidium. The one or more salts of rubidium may be selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$).

In some embodiments, the one or more sources of lithium is one or more lithium salts. The one or more lithium salts may be selected from the group consisting of lithium acetate (CH3COOLi), lithium acetylsalicylate, lithium aspartate, lithium benzoate (C6H5COOLi), lithium bitartrate, lithium bromide (LiBr), lithium carbonate (Li2CO3), lithium chloride (LiCl), lithium chromate (LiCrO4), lithium citrate (Li3C6H5O7), lithium fluoride (LiF), lithium gluconate, lithium iodate (LiIO3), lithium metaborate (LiBO2), lithium nitrate (LiNO3), lithium orotate (LiC5H3N2O4), lithium perchlorate (LiClO4), lithium phosphate (Li3PO4), lithium selenite ($LiH3(SeO3)_2$), lithium succinate (C4H5LiO4), lithium sulfate (Li2SO4), and lithium thenoate.

In some embodiments, the controlled release oral dosage form has a unit dose or amount of cesium of about 10 milligrams to about 1500 milligrams or any specific amount or range as described herein. In some embodiments, the unit dose or amount of cesium is about 20 milligrams, about 40 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, about 1350 milligrams, about 1400 milligrams, about 1450 milligrams, or about 1500 milligrams.

In some embodiments, the controlled release oral dosage form has a unit dose or amount of rubidium of about 10 milligrams to about 1350 milligrams or any specific amount or range as described herein. In some embodiments, the unit dose or amount of rubidium is about 25 milligrams, about 35 milligrams, about 50 milligrams, about 75 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, or about 1350 milligrams.

In some embodiments, the controlled release oral dosage form has a unit dose or amount of lithium of about 0.1 milligrams to about 85 milligrams or any specific amount or range as described herein. In some embodiments, the unit dose or amount of lithium is about 1 milligram, about 1.5 milligrams, about 2 milligrams, about 5 milligrams, about 10 milligrams, about 15 milligrams, about 20 milligrams, about 25 milligrams, about 30 milligrams, about 35 milligrams, about 40 milligrams, about 45 milligrams, about 50 milligrams, about 55 milligrams, about 60 milligrams, about 65 milligrams, about 70 milligrams, about 75 milligrams, about 80 milligrams, or about 85 milligrams.

In some embodiments, the controlled release oral dosage form comprises one or more sources of cesium and one or more sources of rubidium. In some embodiments, the ratio of the amount of cesium to the amount of rubidium ranges from about 1.0 part cesium to 1.0 part rubidium to about 2.0 parts cesium to about 1.0 part rubidium. In some embodiments, the ratio of the amount of cesium to the amount of rubidium ranges from about 1.4 parts cesium to about 1.0 part rubidium to about 1.8 parts cesium to about 1.0 part rubidium. In some embodiments, the ratio of the amount of cesium to the amount of rubidium is about 1.66 parts cesium to about 1.0 part rubidium.

In some embodiments, the controlled release oral dosage form comprises rubidium chloride in an amount of about 50 milligrams to about 1900 milligrams and cesium chloride in an amount of about 50 milligrams to about 1900 milligrams or any amount of rubidium chloride or cesium chloride described herein. In some embodiments, the one or more alkali metals are rubidium chloride in an amount of about 150 milligrams and cesium chloride in an amount of about 250 milligrams. In some embodiments, the one or more alkali metals are rubidium chloride in an amount of about 175 milligrams and cesium chloride in an amount of about 290 milligrams.

In some embodiments, the oral dosage form has a first layer comprising a first part of the one or more alkali metals and a second layer comprising a second part of the one or more alkali metals. In some embodiments, oral dosage form has a first layer comprising a first part of the one or more alkali metals, a second layer comprising a second part of the one or more alkali metals, and a third layer comprising a third part of the one or more alkali metals. In some embodiments, the first layer comprises an outer layer, the second layer comprises a middle layer, and the third layer comprises an inner layer of the dosage form. In dosage forms having two layers, the first layer can be an outer layer and the second layer an inner layer. In some embodiments, the three layers each comprise a region of the dosage form. In some embodiments, the second and/or third layer are embedded within the first layer.

In some embodiments, the controlled release oral dosage can have a first layer comprising about 1-99% by weight of the total content of the one or more alkali metals, a second layer comprising about 1-99% by weight of the total content of the one or more alkali metals, and a third layer comprising about 1-99% by weight of the total content of the one or more alkali metals. In some embodiments, the controlled release oral dosage can have a first layer comprising about 40-50% by weight of the total content of the one or more alkali metals, a second layer comprising about 25-35% by weight of the total content of the one or more alkali metals, and a third layer comprising about 20-30% by weight of the total content of the one or more alkali metals. In some embodiments, the controlled release oral dosage can have a first layer comprising about 45% by weight of the total content of the one or more alkali metals, a second layer comprising about 30% by weight of the total content of the one or more alkali metals, and a third layer comprising about 25% by weight of the total content of the one or more alkali metals. In some embodiments, the controlled release oral dosage can have a first layer comprising about 35%, 36%, 37%, 38%, 39%, 40%, 41%, 42% 43%, 44%, 45%, 46%, 47%, 48%, 49%, 50%, 51%, 52%, 53%, 54% or 55% by weight of the total content of the one or more alkali metals, a second layer comprising about 20%, 21%, 22%, 23%, 24%, 25%, 26%, 27%, 28%, 29%, 30%, 31%, 32%, 33%, 34%, 35%, 36%, 37%, 38%, 39%, or 40% by weight of the total content of the one or more alkali metals, and a third layer comprising about 15%, 16%, 17%, 18%, 19%, 20%, 21%, 22%, 23%, 24%, 25%, 26%, 27%, 28%, 29%, 30%, 31%, 32%, 33%, 34%, or 35% by weight of the total content of the one or more alkali metals.

In some embodiments, the controlled release oral dosage can have a first layer comprising one or more alkali metals that is characterized by being released within about 0-40 minutes after oral ingestion, a second layer comprising one or more alkali metals that is characterized by being released within about 1-16 hours after oral ingestion, and a third layer comprising one or more alkali metals that is characterized by being released within about 5-24 hours after oral ingestion. In some embodiments, the controlled release oral dosage can have a first layer comprising one or more alkali metals that is characterized by being released within about 0-40 minutes after oral ingestion, a second layer comprising one or more alkali metals that is characterized by being released within about 2-12 hours after oral ingestion, and a third layer comprising one or more alkali metals that is characterized by being released within about 8-16 hours after oral ingestion. In some embodiments, the controlled release oral dosage can have a first layer comprising one or more alkali metals the is characterized by being released within about 0-40 minutes after oral ingestion, a second layer comprising one or more alkali metals that is characterized by being released within about 3-5 hours after oral ingestion, and a third layer comprising one or more alkali metals that is characterized by being released within about 6-10 hours after oral ingestion. In some embodiments, the controlled release oral dosage form can have a first layer comprising one or more alkali metals that is characterized by being released within about 0-40 minutes after oral ingestion, a second layer comprising one or more alkali metals that is characterized by being released within about 4 hours after oral ingestion, and a third layer comprising one or more alkali metals that is characterized by being released within about 8 hours after oral ingestion.

In some embodiments, the release profile of one or more of the first, second and third layers of the one or more alkali metals is characterized by a burst release profile. A burst release is well known in the art and it is when a large proportion of the active ingredient (in this case the one or more alkali metals) is quickly released. In some embodiments, each of the first, second and third layers of the one or more alkali metals is characterized by a burst release profile. In some embodiments, the controlled release oral dosage form burst releases the alkali metals after ingestion within 0-40 minutes for the first layer, at about 4 hours for the second layer and at about 8 hours for the third layer. In some embodiments, an individual administered the oral dosage form every 12 hours will receive a substantial dose of alkali metals about every four hours. The inventor has surprisingly found that the most effective treatment for drug addiction and processed food addiction was to copy the burst release process that was used in the addiction problem.

Any suitable means can be used to obtain the controlled release oral dosage of the claimed invention having one or more layers characterized by burst release of the one or more alkali metals. In some embodiments, the controlled release oral dosage form is a tablet, multi particulate, a capsule or a combination thereof. In some embodiments, suitable dosage forms include, but are not limited to:

(a) osmotic potential triggered release forms (e.g. see U.S. Pat. No. 3,952,741), (b) compression coated multi-layer tablets (e.g. see U.S. Pat. No. 5,464,633), (c) capsules containing an erodible plug (e.g. see U.S. Pat. No. 5,474,784), and (d) formulations coated with or containing pH dependent polymers including shellac, phthalate derivatives, polyacrylic acid derivatives and crotonic acid copolymers.

In some embodiments, the controlled release oral dosage form comprises one or more polymers. In some embodiments, the polymer comprises one or more of gelatin, cellulose, a cellulose derivative and combinations thereof.

In some embodiments, the polymer comprises a swellable hydrophilic polymer. Examples of swellable hydrophilic polymers that can be used in the controlled release oral dosage forms of the present invention include vinylpyrrolidone polymers such as povidone, or crosslinked polyvinylpyrrolidone such as crospovidone; cellulose and cellulose derivatives such as microcrystalline cellulose, methylcellulose, ethylcellulose, hydroxypropylcellulose, hydroxypropyl methylcellulose, carboxyalkyl celluloses or crosslinked carboxyalkylcelluloses and their alkali salts; sodium starch glycolate, starch and starch derivatives, ion-exchange resins and mixtures thereof.

In some embodiments, water-soluble compounds suitable for inducing osmosis, i.e. osmotic agents or osmogens, can be used when the alkali metal themselves does not exert sufficient osmotic pressure in order to imbibe fluid from the surroundings. The examples of agents used for inducing osmosis can include inorganic salts such as magnesium chloride or magnesium sulfate, sodium or potassium chloride, sodium or potassium hydrogen phosphate, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like, and mixtures thereof. The amount of osmogents that can be used depends on the particular osmogent that is used.

Means to achieve pH-independent or time-dependent delayed release profiles are known to those skilled in the art, see *Pulsatile Drug Delivery Systems: A Review*, by Gothoskar, A V, Joshi, A M and Joshi, N H, Drug Delivery Technology, June 2004 Vol. 4 Number 5, the disclosure of which is hereby incorporated herein by reference in its entirety. These methods typically involve the use of a coating which: either dissolves or erodes over a certain time period; is subject to enzymatic, bacterial, chemical, or some other form of film degradation over time; or involves a type of swelling and rupturing coating system, typically a semi-permeable film that allows liquid to penetrate into the core of the dosage form thus creating an internal pressure, either from osmosis or effervescence or swelling that results in the catastrophic failure of the film after a certain period of time. Examples of such methods utilizing acrylic polymers are described in EP 0436370 B1, and in U.S. Pat. Nos. 5,395,628 and 6,878,387. Other systems can make use of a plug that does not allow release of the active agent until sufficient force is applied to the plug such that it is expelled.

In some embodiments, a pH-dependent coating can be used. In some embodiments, a change in pH as the dosage form traverses the gastrointestinal tract results in erosion or dissolution of a coating material, which triggers the release of the one or more alkali metals.

In some embodiments, the controlled release oral dosage form can include one or more layers of the one or more alkali metals characterized by a sustained or prolonged release profile of the alkali metals. In some embodiments, the dosage form has a burst or immediate release layer and a sustained or prolonged release layer. In some embodiments, the dosage form has two burst or immediate release layers and one sustained or prolonged release layer. In some embodiments, the dosage form has a multiplicity of burst or immediate release layers and sustained or prolonged release layers.

In some embodiments, the controlled release oral dosage form is a capsule. In some embodiments, the alkali metals are in powder form and are filled in a capsule. In some embodiments, one or more pharmaceutically acceptable excipients are added to the powder. In some embodiments, potassium is added in amounts ranging from about 150 milligrams to about 5000 milligrams. Pharmaceutical excipients can be added to the alkali metals to counteract any discomfort of the alkali properties when ingested, such as, for example, gelatin, or mask any unpleasant taste of the composition. In some embodiments, the one or more alkali metals are adhered to the inside of a capsule wall with a pharmaceutically acceptable adhesive or binder. In some embodiments, adhering the one or more alkali metals to the capsule wall is advantageous for manufacture of the capsule.

In some embodiments, the capsule dosage form has a first layer comprising a first capsule shell, wherein the first capsule shell encapsulates a first part of the one or more alkali metals; a second layer comprising a second capsule shell, wherein the second capsule shell encapsulates a second part of the one or more alkali metals; and a third layer comprising a third capsule shell, wherein the third capsule shell encapsulates a third part of the one or more alkali metals, wherein the third layer is encapsulated inside the second capsule shell and the second layer is encapsulated inside the first capsule shell. In some embodiments, the first capsule shell, the second capsule shell and/or the third capsule shell comprise one or more polymers. In some embodiments, the polymers can include gelatin, cellulose, a cellulose derivative and combinations thereof.

In some embodiments, the one or more polymers of the one or more capsule shells can include hard gelatin or soft gelatin. Soft gelatin capsule wall is composed essentially of gelatin which can be plasticized or which can contain other gelatinous material that retains plasticity without becoming brittle. Hard gelatin capsule wall is composed of gelatin or other gelatinous material with the appearance of having been or chemically plasticized to the extent of retaining in the unfilled or filled condition a specified shape with a near brittle or brittle physical property. Various gelatin capsule walls can be prepared, depending on the fill properties, climatic conditions, and end use. Typically, gelatin formulations include the same basic ingredients, namely, gelatin, a plasticizer such as glycerin, water, and optionally preservatives. Formulations of gelatins are well known.

In some embodiments, one or more layers of the oral dosage form, for example, in the case of capsules, capsule walls, can have a coating on the surface, such as a wax coating, for example, carnauba wax, bees wax, castor wax, candellila wax, paraffin wax, or a combination thereof. The thickness of the wax coating can be varied to control the rate of release of the alkali metals. In some embodiments, the thickness of the coating is 0.1 to 100 micrometers.

In some embodiments, one or more layers of the oral dosage form, for example, in the case of capsules, one or more capsule walls, can have a coating of at least one enteric material that is resistant to dissolution in a time dependent and/or pH dependent manner. In some embodiments, at least one such enteric material is integrated within the capsule wall. An example of an enteric material is a neutral polyacrylate such as poly(ethylacrylate-methylmethacrylate). Suitable capsule wall coating materials include, but are not limited to EUDRAGIT® L30 D-55 and EUDRAGIT® FS30 D, both manufactured by Evonik Industries AG of Darmstadt, Germany. In some embodiments, the one or more alkali metals are formulated as pellets that fill a capsule shell, and the pellets can be coated with one or more enteric materials.

In some embodiments, at least one of the capsule walls can include a cellulose derivative such as cellulose ester, cellulose ether, cellulose citrate, cellulose triacetate, cellulose acetate phthate, methyl cellulose, ethyl cellulose, hydroxypropyl cellulose, hydroxypropyl methylcellulose, and hydroxypropyl methylcellulose phthalate. In some embodiments, the cellulose derivative is hydroxypropyl methylcellulose.

Hydroxypropyl methylcellulose (HPMC), also known as hypromellose, is a semisynthetic, inert, viscoelastic polymer used as an ophthalmic lubricant, as well as an excipient and controlled-delivery component in oral medicaments, found in a variety of commercial products. [See de Silva et al (July 2005) "Hydroxypropyl methylcellulose (HPMC) lubricant facilitates insertion of porous spherical orbital implants". Ophthal Plast Reconstr Surg 21 (4): 301-2; and Williams et al (2001) "Method to recover a lipophilic drug from hydroxypropyl methylcellulose matrix tablets". AAPS PharmSciTech 2 (2): E8]

HPMC has been used as an excipient in oral tablet and capsule formulations, where, depending on the grade, it functions as controlled release agent to delay the release of a medicinal compound into the digestive tract. See Ali Nokhodchi et al. (November 2012) "The Role of Oral Controlled Release Matrix Tablets in Drug Delivery Systems," Bioimpact 2: 175-87. HPMC is also used as a binder and as a component of tablet coatings. See Niazi, Sarfaraz (2004). Handbook of Pharmaceutical Manufacturing Formulations. pp. 275-276. ISBN 9780849317460.

HPMC is a solid, and is a slightly off-white to beige powder in appearance and can be formed into granules. HPMC forms colloids when dissolved in water. This nontoxic ingredient is combustible and can react vigorously with oxidising agents. HPMC in an aqueous solution, unlike methylcellulose, exhibits a thermal gelation property. That is, when the solution heats up to a critical temperature, the solution congeals into a non-flowable but semi-flexible mass. Typically, this critical (congealing) temperature is inversely related to both the solution concentration of HPMC and the concentration of the methoxy group within the HPMC molecule (which in turn depends on both the degree of substitution of the methoxy group and the molar substitution). That is, the higher the concentration of the methoxy group, the lower the critical temperature. The inflexibility/viscosity of the resulting mass, however, is directly related to the concentration of the methoxy group (the higher the concentration, the more viscous or less flexible the resulting mass is). HMPC have grades indicating viscosity.

In some embodiments, the capsule shell of the first layer comprises soft gelatin, the capsule shell of the second layer comprises hard gelatin and a wax coating, and the capsule shell of the third layer comprises hydroxypropyl methylcellulose and a wax coating. The one or more alkali metals of the first layer, second layer or third layer can be mixed with a binder such as a pharmaceutical starch and/or wax, such as pharmaceutically acceptable carnuba wax. In some embodiments, the capsule shell of the first layer comprises soft gelatin, the capsule shell of the second layer comprises hard gelatin and a wax coating, the second layer comprises one or more alkali metals mixed with wax such as carnuba wax, and the capsule shell of the third layer comprises hydroxypropyl methylcellulose and a wax coating. In some embodiments, the one or more alkali metals are attached to capsule shell with a pharmaceutically acceptable adhesive.

In some embodiments, the capsule shell of the first layer comprises soft gelatin, the capsule shell of the second layer comprises HPMC and a poly(ethylacrylate-methylmethacrylate) coating, and the capsule shell of the third layer comprises hydroxypropyl methylcellulose and a poly(ethylacrylate-methylmethacrylate) coating. In some embodiments, the one or more alkali metals are attached to the capsule shell with pharmaceutically acceptable adhesive.

In some embodiments, at least one of the layers of the capsule can comprise particles with a part of the one or more alkali metals. The particles can include excipients controlling the release profile for the one or more alkali metals. In some embodiments, the capsule of the present invention can have a single capsule shell encapsulating two or more types of particles each containing a portion of the one or more alkali metals. Each type of particle can include excipients providing a different release profile for the one or more alkali metals.

In some embodiments, the dosage form of the present invention in the form of a capsule can be characterized by any of the release profiles discussed herein for the controlled release oral dosage form. In some embodiments, the first part of the one or more alkali metals is characterized by a release profile that is faster than the second part of the one or more alkali metals and the second part of the one or more alkali metals is characterized by a release profile that is faster than the third part of the one or more alkali metals. In some embodiments, the first part of the one or more alkali metals is characterized by a burst release at about 0-40 minutes after ingestion, the second part of the one or more alkali metals is characterized by a burst release at about 4 hours after ingestion, and the third part of the one or more alkali metals is characterized by a burst release at about 4 hours after ingestion.

Figure 1:
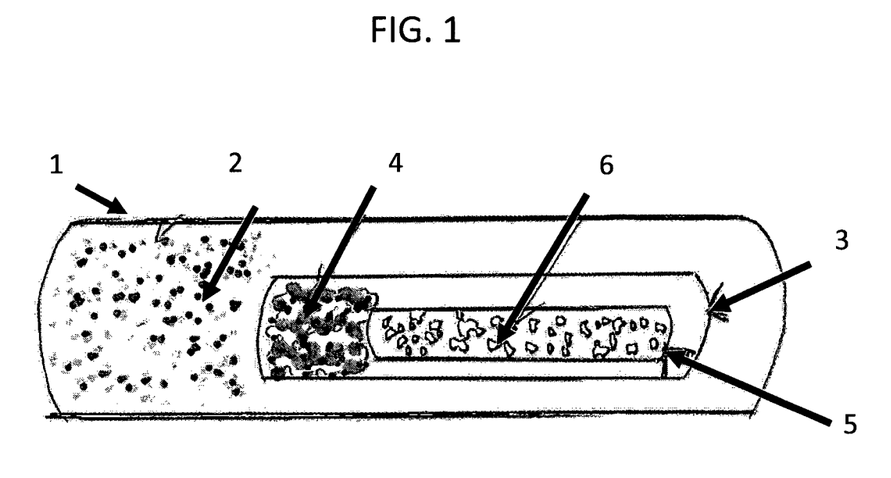
FIG. 1 shows an exemplary controlled release capsule comprising one or more alkali metals.

An embodiment of a capsule of the present invention is shown in FIG. 1. The capsule dosage form of FIG. 1 has a first layer comprising a first capsule shell 1, wherein the first capsule shell encapsulates the first part of the one or more alkali metals 2; a second layer comprising a second capsule shell 3, wherein the second capsule shell encapsulates the second part of the one or more alkali metals 4; and a third layer comprising a third capsule shell 5, wherein the third capsule shell encapsulates the third part of the one or more alkali metals 6. In the capsule shell of FIG. 1, one or more alkali metals 2 are mixed with a binder and compacted at one end of first capsule shell 1.

In some embodiments, the controlled release oral dosage form is a tablet. An oral dosage form in the form of a tablet can be prepared using any suitable pharmaceutical carrier(s) routinely used for preparing solid formulations. Examples of such carriers include magnesium stearate, starch, lactose, sucrose and microcrystalline cellulose.

In some embodiments, the tablet comprises two or more layers each having a part of the one or more alkali metals. The tablet can comprise two, three, four, five, six, seven, eight, nine or ten layers. The layers can be surrounded by another layer. The layers can also form separate regions of the tablet. Each layer can include excipients as discussed herein to delay the release of a part of the one or more alkali metals.

In some embodiments, the tablet comprises a first layer comprising a first part of the one or more alkali metals, a second layer comprising a second part of the one or more alkali metals, and a third layer comprising a third part of the one or more alkali metals, wherein the third layer and the second layer are surrounded by the first layer. In other embodiments, the tablet can be comprised of two or more types of particles each containing a portion of the one or more alkali metals. Each type of particle can include excipients discussed herein providing a different release profile for the one or more alkali metals. The particles can be intermixed or separated into regions or layers.

In some embodiments, at least one of the first layer, the second layer, and the third layer of the tablet of the present invention comprises a polymer. Examples of suitable polymers are described herein. Other suitable polymers are known in the art. In some embodiments, at least one of the first layer, the second layer, and the third layer of the tablet of the present invention comprises swellable hydrophilic polymers described herein.

In some embodiments, at least one of the layers of the tablet of the present invention comprises hydroxypropyl methylcellulose. In some embodiments, at least two of the layers comprise a hydroxypropyl methylcellulose with at least one different property selected from the group consisting of methoxy content, hydroxypropoxyl content, molecular weight and viscosity. In some of the embodiments of the present invention, the second layer and the third layer, but not the first layer, each comprise a polymer that controls release of the one or more alkali metals. In some embodiments, the polymer of the second and third layer is each a different grade of HPMC.

In some embodiments, the tablets of the present invention can comprise a coating on the surface of one or more of the layers. The coating can be a wax or enteric material as described above. In some embodiments, the second and/or third layer is coated with a wax or enteric material. In some embodiments, the second and third layer are coated with poly(ethylacrylate-methylmethacrylate). Examples of suitable poly(ethylacrylate-methylmethacrylate) are described herein.

In some embodiments, the tablets of the present invention can comprise layers comprising pharmaceutically acceptable carriers, excipients and/or diluents as described herein. The ratio of the pharmaceutically acceptable carriers, excipients and/or diluents to the one or more alkali metals and/or other components of the layers of the tablet may be varied to control the physical properties of the tablet such as compressibility and hardness. Acceptable ratios of the pharmaceutically acceptable carriers, excipients and/or diluents to the one or more alkali metals and/or other components of the layers of the tablet include, but are not limited to, a range of about 10:1 to 1:10. In some embodiments, the ratio of the pharmaceutically acceptable carriers, excipients and/or diluents to the one or more alkali metals and/or other components of the layers of the tablet is about 2:1, 1:1 and 1:2. Other ratios can be used in the present invention and are not limited.

In some embodiments, the first layer of the tablet of the present invention comprises a first layer comprising a first part of the alkali metals and pharmaceutically acceptable excipients, a second layer embedded within the first layer and comprising HPMC and a second part of the one or more alkali metals, and a third layer also embedded within the first layer and comprising HPMC and a third part of the one or more alkali metals. By adjusting the grade of HPMC and the weight ratio of HPMC to the one or more alkali metals, the release profile for the alkali metals can be adjusted. In some embodiments, the weight ratio of HPMC to the part of one or more alkali metals is between about 1:10 and 10:1. In other embodiments, the weight ratio of HPMC to the part of one or more alkali metals is between about 2:10 and 6:10. In other embodiments, the weight of HPMC is about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% of the weight of the corresponding part of one or more alkali metals. In some embodiments, the weight of HPMC is about 40% to 45% of the weight of the corresponding part of one or more alkali metals. Any suitable HPMC giving the desired release profile can be used in the present invention. In some embodiments, METHOCEL CR grade Polymers (K100M) or METHOCEL CR grade Polymers (K15M) can be used.

In some embodiments, the tablet of the present invention comprises
  a. a first layer comprising about 45% by weight of the total one or more alkali metals of the tablet and pharmaceutically acceptable excipients;
  b. a second layer embedded within the first layer and comprising HPMC and about 30% by weight of the one or more alkali metals of the tablet, wherein the weight ratio of HPMC to the one or more alkali metals of the second layer is about 4:10; and
  c. a third layer also embedded within the first layer and comprising HPMC and about 25% of the one or more alkali metals of the tablet, wherein the weight ratio of HPMC to the one or more alkali metals of the second layer is about 45:100.

In some embodiments, the total weight of the one or more alkali metals in the tablet is about 150 milligrams of rubidium chloride and about 250 milligrams of cesium chloride. In other embodiments, the total weight of the one or more alkali metals in the tablet is about 175 milligrams of rubidium chloride and about 290 milligrams of cesium chloride. The total weight of the one or more alkali metals in the tablet can include any weight described herein. The weight of each alkali metal of the one or more alkali metals in the tablet can include any weight described herein.

The controlled oral dosage of the present invention in the form of a tablet can be characterized by any of the release profiles of the one or more alkali metals described herein. In some embodiments, the first part of the one or more alkali metals is characterized by a release profile that is faster than the second part of the one or more alkali metals and the second part of the one or more alkali metals is characterized by a release profile that is faster than the third part of the one or more alkali metals. In some embodiments, the first part of the one or more alkali metals is characterized by release at about 0-40 minutes after ingestion, the second part of the one or more alkali metals is characterized by release at about 4 hours after ingestion, and the third part of the one or more alkali metals is characterized by release at about 4 hours after ingestion.

Figure 2:
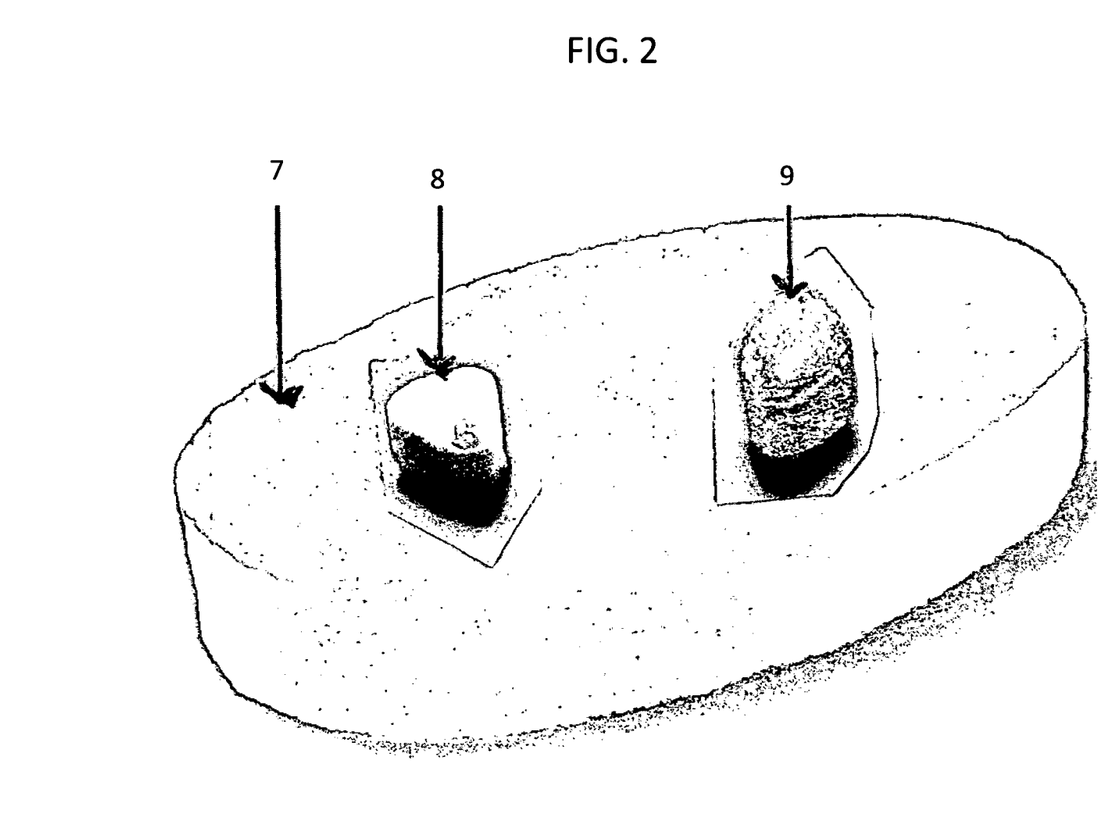
FIG. 2 shows an exemplary controlled release tablet comprising one or more alkali metals.

FIG. 2 is an example of the components of a completed tablet of the present invention. The first layer 7 comprises 45% of the total weight of the one or more alkali metals and an equal weight of high performance pharmaceutical binders (such as starch). First layer 7 can be compacted at high levels and contain second layer 8 and third layer 9. Second layer 8 comprises 30% of the total weight of the one or more alkali metals mixed with HPMC medium viscosity K15M (Methocel K15M, Dow Chemical). Third layer 9 comprises 25% of the total weight of the one or more alkali metals mixed with HPMC high viscosity grade K100M (Methocel K100M, Dow Chemical). In a tablet of the present invention, second layer 8 and third layer 9 would be contained within first layer 7.

The present invention further includes methods of treating drug addiction in a subject in need thereof, comprising administering to the individual a controlled release oral dosage form of the invention. The dosage form can be administered 1, 2, 3, 4, 5, 6, 7, 8, 9, 10, 11, or 12 times per day. In some embodiments, the dosage form is administered 4 times a day, 2 times a day, or once per day. In some embodiments, the dosage form is administered every 2 hours, every 4 hours, every six hours, every 8 hours, every 10 hours, every 12 hours or every 24 hours. In some embodiments, the dosage form is administered twice a day (every 12 hours).

In some embodiments, the dosage form comprises a unit dose or amount of rubidium chloride of about 50 milligrams to about 1900 milligrams and cesium chloride of about 50 milligrams to about 1900 milligrams. In some embodiments, the dosage form comprises a unit dose or amount of rubidium chloride of about 150 milligrams and cesium chloride of about 250 milligrams. In some embodiments, the dosage form comprises a unit dose or amount of rubidium chloride of about 175 milligrams and cesium chloride of about 290 milligrams. In some embodiments, the dosage form comprises a unit dose or amount of rubidium chloride of about 50 milligrams to about 1900 milligrams and cesium chloride of about 50 milligrams to about 1900 milligrams. In some embodiments, the dosage form comprises a unit dose or amount of rubidium chloride of about 150 milligrams and cesium chloride of about 250 milligrams. In some embodiments, the dosage form comprises a unit dose or amount of rubidium chloride of about 175 milligrams and cesium chloride of about 290 milligrams.

In some embodiments, the dosage form comprises one or more salts of cesium having a combined content in an amount of about 40 milligrams to about 1500 milligrams or any specific amount or range as described herein; one or more salts of rubidium having a combined rubidium content in an amount of about 35 milligrams to about 1350 milligrams or any specific amount or range as described herein; one or more lithium salts having a combined lithium content in an amount of about 0.3 milligrams to about 85 milligrams or any specific amount or range as described herein; and combinations thereof.

The duration of administration of the controlled release oral dosage form can vary for each individual to be treated/administered depending on the individual cases and the strength of the addiction. In some embodiments, the controlled release oral dosage form can be administered continuously for a period of several days, weeks, months, or years of treatment or can be intermittently administered where the individual is administered the dosage form for a period of time, followed by a period of time where they are not treated, and then a period of time where treatment resumes as needed to suppress drug addiction in the individual. For example, in some embodiments, the individual to be treated is administered the controlled release oral dosage form of the invention daily, every other day, every three days, every four days, 2 days per week 3 days per week, 4 days per week, 5 days per week or 7 days per week. In some embodiments, the individual is administered the controlled release oral dosage form for 1 week, 2 weeks, 3 weeks, 4 weeks, 1 month, 2 months, 3 months, 4 months, 5 months, 6 months, 7 months, 8 months, 9 months, 10 months, 11 months, 1 year or longer. In some embodiments, the individual is administered the controlled release oral dosage form every morning with or after food and taken for two months until the addiction to the drug is lost. In some embodiments, individuals who are obese are administered the controlled release oral dosage form of the invention every day for longer durations of time. In some embodiments, drug addicted patients are treated for 6 months or longer to achieve the desired effect.

All references cited herein are specifically incorporated in their entirety unless otherwise indicated.

The present invention may be better understood by reference to the following non-limiting Examples, which are provided as exemplary of the invention. The following examples are presented in order to more fully illustrate some embodiments of the invention. They should in no way be construed, however, as limiting the broad scope of the invention.

EXAMPLES

Example 1

A blind trial with 300 mg of rubidium chloride taken once per day in a 90 kg male to treat codeine addiction The trial below was a blind trial with 300 mg of rubidium chloride taken once per day administered in a glass of water in the morning by a male of 90 kg; and a placebo being taken by a woman of 66 kg, both of whom were addicted to codeine The female had no effect over the two month trial but the male indicated that the stimulation from the medication he took was very, very strong and he had more get-up-and-go and less craving for the drug than normal even after the first day.

He also stated he had much more energy than before and was much more active during the day with the "medication."

The trial was undertaken with the recommendation by doctors not to proceed too quickly and to eat potassium rich foods, especially at night; The most difficult aspect was to stop the craving in the evening—a solution for people who cannot stop the craving at night would be to split the dosage of the 300 mg of Rubidium Chloride and take half in the morning and half late in the afternoon.

The aim of this trial was to stop the craving for codeine with the aid of the compound and use the enhanced energy and stimulation supplied from the compound that was tested to change addiction habits.

The trial was for 300 mg of Rubidium Chloride taken once per day taken in a glass of water in the morning by the male in this blind study and a placebo of powdered sugar taken by a female once per day taken in a glass of water in the morning.

The trial lasted two months and during this time period the male lost the addiction to codeine.

Example 2

A trial with 150 mg of rubidium chloride and 150 mg cesium chloride taken once per day in a 98 kg male to treat methamphetamine addiction The trial below was a blind trial with 150 mg of rubidium chloride and 150 mg of cesium chloride taken once per day taken in a glass of water in the morning by a male of 98 kg; and a placebo being taken by a woman of 66 kg—both of whom were addicted to methamphetamine.

The female had no effect over the two month trial but the male indicated that the stimulation from the medication he took was very strong and he had less craving than normal even after the first day.

The trial was undertaken with the recommendation by doctors not to proceed too quickly and to eat potassium rich foods, especially at night; The most difficult aspect was to stop the craving in the evening—a solution for people who cannot stop the craving at night would be to split the dosage of the 300 mg and take half in the morning and half late in the afternoon.

The male in this trial subsequently stated it may be advisable to give 150 mg of rubidium chloride and 150 mg of cesium chloride in the evening as well.

The aim of this trial was to stop the craving for methamphetamine with the aid of the compounds and use the enhanced energy and stimulation supplied from the compound that was tested to change addiction habits.

The trial was for 150 mg of rubidium chloride and 150 mg of cesium chloride taken once per day taken in a glass of water in the morning by the male in this blind study and a placebo of powdered sugar taken by a female once per day taken in a glass of water in the morning.

The trial lasted two months and during this time period the male lost the addiction to methamphetamine.

The male in this trial stated when the trial was finished it would be advisable to give 150 mg of rubidium chloride and 150 mg of cesium chloride in the evening as well to stop the symptoms of the addiction.

Example 3

A trial with 150 mg of rubidium chloride and 250 mg cesium chloride taken twice per day in a 102 kg male to treat methamphetamine addiction.

The trial below was a blind trial with 150 mg of rubidium chloride and 250 mg of cesium chloride taken twice per day taken in a glass of water in the morning by a male of 102 kg; and a placebo being taken by a male of 86 kg—both of whom were addicted to methamphetamine.

This particular mixture of 150 mg of rubidium chloride and 250 mg of cesium chloride taken twice per day was for drug addiction and worked by far the best of the many trials undertaken and the many different formulations that were tested.

The male of 86 kg had no effect over the four month trial but the 102 kg male indicated that the stimulation from the medication he took was very strong and he had less craving than normal even after the first day.

The trial was undertaken with the recommendation by doctors to eat potassium rich foods, especially at night;

The aim of this trial was to stop the craving for methamphetamine and with the aid of the compounds to change addiction habits.

The trial was for 150 mg of rubidium chloride and 250 mg of cesium chloride taken twice per day taken in a glass of water in the morning by the 102 kg male in this blind study and a placebo of powdered sugar taken by a 86 kg male twice per day taken in a glass of water.

The trial lasted four months and during this time period the 102 kg male lost the addiction to methamphetamine.

This particular mixture of 150 mg of rubidium chloride and 250 mg of cesium chloride taken twice per day for drug addiction over four months is new and novel and worked extremely well.

Example 4

A trial with 175 mg of rubidium chloride and 290 mg cesium chloride taken twice per day in a 142 kg male to treat addiction to highly processed foods.

The trial below was a blind trial with 175 mg of rubidium chloride and 290 mg of cesium chloride taken twice per day taken in a glass of water in the morning by a male of 142 kg; and a placebo being taken by a male of 129 kg—both of whom were addicted to highly processed foods.

This particular mixture of 175 mg of rubidium chloride and 290 mg of cesium chloride taken twice per day for addiction worked by far the best of the many trials that were undertaken.

The male of 129 kg had no effect over the four month trial but the 142 kg male indicated that the stimulation from the medication he took was very strong and he had less craving than normal even after the first day.

The trial was undertaken with the recommendation by doctors to eat potassium rich foods, especially at night;

The aim of this trial was to stop the craving for highly processed foods and with the aid of the compounds to change addiction habits. The trial was for 175 mg of rubidium chloride and 290 mg of cesium chloride taken twice per day taken in a glass of water in the morning by the 142 kg male in this blind study and a placebo of powdered sugar taken by a 129 male twice per day taken in a glass of water.

The trial lasted four months and during this time period the 142 kg male lost the addiction to highly processed foods This particular mixture of 175 mg of rubidium chloride and 290 mg of cesium chloride taken twice per day for highly processed foods addiction over four months is new and novel and worked extremely well.

Example 5

Liquid Composition:
Rubidium Chloride 300 mg
Potassium Chloride: 300 mg.
Diluted in 150 ml of water If desired, a flavoring agent such as TRUSIL LEMON ELITE (the trade name of a commercial lemon flavoring agent supplied by Bush, Boake & Allan), may be incorporated in the mixture to provide a particularly pleasant flavor on the palate. Artificial sweeteners, colorings and preservatives may likewise be incorporated.

Example 6

Liquid Composition:

A first mixture (mixture A) was prepared by blending 500 mg of disodium hydrogen phosphate ($Na_2HPO_4.12H_2O$) with 5 g of sucrose and 3 g of dextrose.

A second mixture (mixture B) was prepared by blending together the following ingredients in the stated amounts:
Rubidium Chloride: 300 mg
Potassium Chloride: 300 mg
Magnesium Sulfate: 150 mg
Sodium Citrate: 120 mg
Sodium Acid Phosphate: 110 mg
Ascorbic Acid: 100.0 mg
Pyridoxine Hydrochloride: 25.0 mg
Citric Acid: 450 mg
Sodium Chloride: 70 mg The two mixtures were then blended together and milled to 100 mesh to form a drink concentrate.

If desired, a flavoring agent such as TRUSIL LEMON ELITE (the trade name of a commercial lemon flavoring agent supplied by Bush, Boake & Allan), may be incorporated in the mixture to provide a particularly pleasant flavor on the palate. Artificial sweeteners, colorings and preservatives may likewise be incorporated.

Example 7

As shown in FIG. 1, an outer soft gelatin first capsule shell 1 was used and the first part of the one or more alkali metals 2 having 45 percent of the alkali metals was placed in capsule shell 1 with a binder (a pharmaceutical starch) to allow the compound to be compressed and to remain in place in capsule shell 1.

Thereafter a smaller hard gelatin second capsule shell 3 was used and the second part of the one or more alkali metals 4 having 30 percent of the alkali metals was placed in second capsule shell 3 and second capsule shell 3 was coated in a pharmaceutical wax (carnuba wax) to delay release for four hours. Mixing the 30 percent of the compound with a pharmaceutical wax such as carnuba wax was also found to help to ensure the achievement of a four hour delay in release of the alkali metals.

Another effective way of delaying release for four hours was to coat the outside of a second capsule shell comprising HPMC (Size 0 capsules from Capsugel Division of Pfizer Inc.) with Eudragit® L 30 D-55. This was very effective as the outside of the HPMC capsule was seen to be rough in character and the Eudragit® L 30 D-55 adhered very well. This second capsule shell comprising HPMC with Eudragit@ L 30 D-55 contained 30 percent of the total alkali metals and the second capsules were sealed with the LEMS™ process (Cole, 2000) using a modified sealing fluid. After the coating process, the capsules were dried on trays for 2 hours at 30° C. (See Cole, E. T., 2000. Liquid filled and sealed hard gelatin capsules. Capsugel Technical Bulletin.)

Thereafter a smaller third capsule shell 5 comprising HPMC (from Capsugel Division of Pfizer Inc.) was used and the third part of the one or more alkali metals 6 comprising 25 percent of the alkali metals was placed in the third capsule shell 6. Third capsule shell 6 was coated with Eudragit® FS 30 D to delay release for eight hours. This was very effective as the outside of the HPMC capsule was seen to be rough in character and the Eudragit® FS 30 D adhered very well. After the coating process the capsules were dried on trays for 2 hours at 30° C. The capsules were sealed with the LEMS™ process (Cole, 2000) using a modified sealing fluid. (See Cole, E. T., 2000. Liquid filled and sealed hard gelatin capsules. Capsugel Technical Bulletin.)

Example 8

A tablet with a first layer comprising 45% of the total weight of the one or more alkali metals and an equal weight of high performance pharmaceutical binders (such as starch) was manufactured. This first layer can be compacted at high levels and contain a second layer and a third layer in separate regions of the first layer. The second layer comprises 30% of the total weight of the one or more alkali metals mixed with HPMC medium viscosity K15M (Methocel K15M, Dow Chemical). The HPMC K15M was added at a weight ratio of 4:10 to the weight of the alkali metals. The third layer comprises 25% of the total weight of the one or more alkali metals mixed with HPMC high viscosity grade K100M (Methocel K100M, Dow Chemical). The HPMC K100M was added at a weight ratio of 45:100 to the weight of the alkali metals. The components of Example 8 are shown in FIG. 2.

While there have been shown and described what are presently believed to be certain embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A method of treating drug addiction in an individual human in need thereof, comprising administering to the individual per 24 hour period an effective amount of one or more alkali metals selected from the group consisting of one or more sources of cesium, one or more sources of rubidium, and combinations thereof, wherein the one or more alkali metals are formulated in 1-6 unit dosage forms, wherein the unit dosage forms include a pharmaceutically acceptable carrier, excipient, or diluent, wherein the one or more sources of cesium administered has a total cesium content in an amount of about 40 milligrams to about 1500 milligrams, and the one or more sources of rubidium administered has a total rubidium content in an amount of about 35 milligrams to about 1350 milligrams, wherein the unit dosage form is administered 1-6 times per day.

2. The method of claim 1, wherein the source of cesium is one or more salts of cesium.

3. The method of claim 2, wherein the one or more salts of cesium is selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$).

4. The method of claim 1, wherein the one or more sources of rubidium is one or more salts of rubidium.

5. The method of claim 4, wherein the combined content of rubidium in the one or more salts of rubidium is in an amount of about 35 milligrams to about 1350 milligrams.

6. The method of claim 4, wherein the one or more salts of rubidium is selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$).

7. A method of treating drug addiction in a subject in need thereof, comprising administering to the subject a controlled release oral dosage form comprising an effective amount of one or more alkali metals, comprising a first layer comprising a first part of the one or more alkali metals and a second layer comprising a second part of the one or more alkali metals, wherein the one or more alkali metals comprises one or more sources of cesium and one or more sources of rubidium, wherein the dosage form comprises a unit dose or amount of rubidium chloride of about 50 milligrams to about 1900 milligrams and cesium chloride of about 50 milligrams to about 1900 milligrams, wherein at least one of the layers is characterized by an immediate release profile or a burst release profile.

8. The method of claim 7, wherein the dosage form is administered 1-6 times per day.

9. The method of claim 8, wherein the dosage form is administered twice a day.

10. The method of claim 7, wherein the dosage form further comprises a third layer comprising a third part of the one or more alkali metals.

11. The method of claim 7, wherein the dosage form is a capsule.

12. The method of claim 1, wherein the unit dosage form is in the form of an oral solution.

13. The method of claim 1, wherein the pharmaceutically acceptable carrier, excipient, or diluent is selected from the group consisting of pharmaceutical grade starch, mannitol, lactose, magnesium stearate, sodium saccharin, talcum, cellulose, glucose, sucrose or other sugar, magnesium carbonate, gelatin, oil, alcohol, detergents, emulsifiers and water.

* * * * *